US011638599B2

(12) United States Patent
Schlenker

(10) Patent No.: US 11,638,599 B2
(45) Date of Patent: May 2, 2023

(54) BONE-ANCHORING DEVICE FOR A PEDICLE ACCESS

(71) Applicant: MIMEO Medical GmbH, Filderstadt (DE)

(72) Inventor: Heiter-Julian Schlenker, Karlsruhe (DE)

(73) Assignee: MIMEO MEDICAL GmbH, Filderstadt (DE)

( * ) Notice: Subject to any disclaimer, the term of this patent is extended or adjusted under 35 U.S.C. 154(b) by 0 days.

(21) Appl. No.: 17/429,272

(22) PCT Filed: Jan. 24, 2020

(86) PCT No.: PCT/DE2020/000008
§ 371 (c)(1),
(2) Date: Aug. 6, 2021

(87) PCT Pub. No.: WO2020/160722
PCT Pub. Date: Aug. 13, 2020

(65) Prior Publication Data
US 2022/0087724 A1    Mar. 24, 2022

(30) Foreign Application Priority Data
Feb. 9, 2019  (DE) .................... 10 2019 000 965.7

(51) Int. Cl.
A61B 17/70    (2006.01)
A61B 17/86    (2006.01)
A61B 90/00    (2016.01)

(52) U.S. Cl.
CPC ........ *A61B 17/7098* (2013.01); *A61B 17/704* (2013.01); *A61B 17/7037* (2013.01);
(Continued)

(58) Field of Classification Search
CPC ........ A61B 17/8625; A61B 2017/8655; A61B 17/846; A61B 17/7037
See application file for complete search history.

(56) References Cited

U.S. PATENT DOCUMENTS 5,300,074 A * 4/1994 Frigg .................. A61B 17/725
606/70
6,409,730 B1   6/2002 Green et al.
(Continued)

FOREIGN PATENT DOCUMENTS

DE   197 20 782    11/1998
DE   203 18 732    2/2004
(Continued)

OTHER PUBLICATIONS

International Search Report issued in PCT/DE2020/000008 dated May 25, 2020 (8 pages).
(Continued)

*Primary Examiner* — David W Bates
(74) *Attorney, Agent, or Firm* — Nixon & Vanderhye P.C.

(57) ABSTRACT

A bone anchoring device for anchoring and fixing vertebrae and for insertion into a pedicle canal is disclosed. A fork head having a U-shaped cut-out in a side view for a correction element, a connecting rod with two legs which terminate proximally and form a threaded section which engages with an adjusting means, wherein the legs have a radially outer circumferential area in which at least one retaining groove or other instrument attachment point is formed for gripping the fork head by a handling instrument, and a bone anchoring element with a proximal end facing away therefrom in the axial direction such that a distal direction and a proximal direction are also defined. The bone anchoring element has a spherical head at the proximal area, and the bone anchoring element is polyaxially pivotable with respect to the fork head, and has a pressure piece
(Continued)

distally partially surrounds the bone anchoring element at the ball head, and proximally forms a seat for the connecting rod.

20 Claims, 14 Drawing Sheets

(52) U.S. Cl.
CPC .......... *A61B 17/863* (2013.01); *A61B 17/864* (2013.01); *A61B 17/866* (2013.01); *A61B 90/08* (2016.02); *A61B 2017/8655* (2013.01); *A61B 2090/0811* (2016.02)

(56) References Cited

U.S. PATENT DOCUMENTS

| | | | |
|---|---|---|---|
| 9,125,696 B2 | 9/2015 | Linke | |
| 2003/0083663 A1* | 5/2003 | Goldhahn | A61B 17/68 606/291 |
| 2004/0068258 A1* | 4/2004 | Schlapfer | A61B 17/70 606/311 |
| 2006/0271053 A1* | 11/2006 | Schlapfer | A61B 17/70 606/301 |
| 2009/0192512 A1* | 7/2009 | Sommers | A61B 17/68 606/62 |
| 2010/0331895 A1* | 12/2010 | Linke | A61B 17/86 606/301 |
| 2012/0046698 A1* | 2/2012 | Kolb | A61B 17/864 606/304 |
| 2012/0143266 A1 | 6/2012 | Jackson et al. | |
| 2014/0066991 A1* | 3/2014 | Marik | A61B 17/8625 606/279 |
| 2014/0277159 A1 | 9/2014 | Spratt et al. | |
| 2017/0367836 A1* | 12/2017 | Cardon | A61F 2/4081 |
| 2020/0222088 A1* | 7/2020 | Kraus | A61B 17/8625 |
| 2021/0244455 A1* | 8/2021 | Castro | A61B 17/7035 |

FOREIGN PATENT DOCUMENTS

| | | |
|---|---|---|
| EP | 2 740 428 | 6/2014 |
| EP | 2 732 782 | 2/2018 |
| WO | WO 98/05263 | 2/1998 |
| WO | 98/52482 | 11/1998 |
| WO | WO 98/51241 | 11/1998 |
| WO | WO 02/45606 | 6/2002 |
| WO | 2009/068021 | 6/2009 |
| WO | 2011/054124 | 5/2011 |
| WO | 2018/183830 | 10/2018 |

OTHER PUBLICATIONS

Written Opinion of the International Searching Authority issued in PCT/DE2020/000008 dated May 25, 2020 (11 pages).

Shah Furqan, et al., "30 printed Ti6Al4V implant surface promotes bone maturation and retains a higher density of less aged osteocytes at the bone-implant interface", Acta Biomaterialia, vol. 30, pp. 357-367 (2016).

DePuy Synthes, "Click'X System. The complete top-loading pedicle screw and rod system for the posterior stabilization of the lower back", Surgical Technique, 52 pages (Nov. 2015).

DePuy Synthes, "Click'x Perforiert, Augmentierbare Pedikelschrauben für osteoporatische Knochen", Description of the surgical techniques for the Click'X System from DePuy Synthes, 20 pages (Aug. 2016).

Zintel Irene et al., "AO ASIF Principles in Spine Surgery", Springer, Chapter 8, p. 186 (1998).

Lin Li-Chun, et al., "A biomechanical study of the cortex-anchorage vertebral screw", Clinical Biomechanics, vol. 18, pp. S25-S32 (2003).

Shah Furqan, et al., "30 printed Ti6Al4V implant surface promotes bone maturation and retains a higher density of less aged osteocytes at the bone-implant interface", Acta Biomaterialia, vol. 30, pp. 357-367 (2016).

* cited by examiner

BONE-ANCHORING DEVICE FOR A PEDICLE ACCESS

CROSS REFERENCE TO RELATED APPLICATIONS

The present application is a National Phase of International Application Number PCT/DE2020/000008 filed Jan. 14, 2020, which designated the U.S. and claims priority benefits from German Application Number DE 10 2019 000 965.7 filed Feb. 9, 2019, the entire contents of each of which are hereby incorporated by reference.

In the case of structurally weakened spinal columns, a biomechanical problem can arise during fixation with bone anchors, namely that the bone is not sufficiently load-bearing for adequate anchoring with pedicle screws or the like. For this purpose, augmentation with bone cement of the vertebra is considered state of the art. A functioning alternative to pedicle screws with bone cement cannot be found in the current state of the art.

Bone cement is based on polymethyl methacrylate (PMMA), is mixed from two components during the operation, and is available for use for just a few minutes. Curing during application and injection produces higher temperatures, such that the risk of overheating of the tissue cannot be ruled out. This can result in necrosis. Furthermore, there is an active risk of triggering a life-threatening embolism during the injection, e.g. as soon as liquid PMMA enters the bloodstream and hardens. Unintentional wetting of other critical structures (e.g. dura or nerve roots) with PMMA is also possible and therefore poses a risk. Once injected, the hardened PMMA plastic can no longer be removed out of the bone. There are more difficult conditions for a revision, so it would be good to do without bone cement.

U.S. Pat. No. 5,300,074A shows a concept for the treatment of femoral fractures in which a helical blade is used for the rotationally stable fixation of a femoral head fracture. WO9805263A1 shows a similar concept, wherein further biomechanical advantages of a bell-like implant are discussed here. Another biomechanical advantage can be seen from the descriptions and the illustrated structures of both documents. The plate in the femoral head, which is oriented distally and angled at approx. 90°, is rotated exactly in the direction of the load, such that maximum bone surface contact is generated in the direction of the load. This fixation method is particularly suitable for structurally weaker bones.

A blade-like bone anchor for stabilizing spinal column segments was designed for the anterior or antero-lateral approach (WO0245606A1). The bone anchor presented there, however, is not suitable for posterior access through a pedicle canal. The applicant demands a special insertion orientation for this bone anchor, which is not suitable for implantation in the pedicle canal. It is postulated that the distal blade orientation of the bone anchor is aligned parallel to the medial-lateral or distal-proximal plane and then implanted in the vertebra. However, this orientation does not permit implantation in a pedicle canal, as this canal has a different main orientation. Furthermore, the structure presented there is made up of multiple parts, which has an adverse effect on fatigue strength.

It is the object of the bone anchoring device according to the invention to offer an alternative to cement-augmented pedicle screws, especially as soon as the inner bony structure of the vertebra is weakened due to osteopenia or even osteoporosis. Furthermore, working with pedicle anchors should be simplified and accelerated for the surgeon by the type of insertion.

According to the invention, this object is achieved by a bone anchoring device for anchoring and fixing vertebrae, in particular for insertion into a pedicle canal. The bone anchoring device furthermore has a fork head, which is U-shaped in a side view, for a correction element, in particular a connecting rod, with two legs which terminate proximally and form a threaded section which engages with an adjusting means, wherein the legs have a radially outer circumferential area in which at least one retaining groove or other instrument attachment point is formed for gripping the fork head by means of a handling instrument, and a bone anchoring element with a spherical head, and the bone anchoring element can be pivoted polyaxially with respect to the fork head, and has a pressure piece, wherein the pressure piece distally partially surrounds the bone anchoring element at the ball head, and proximally forms a seat for the connecting rod, and the bone anchoring element, coming from the distal direction, is mounted with the fork head and with the pressure piece, characterized in that the bone anchoring element has a mainly cylindrical core, and two wings extending laterally, and in that the wings have a distal wing orientation and a different proximal wing orientation, and in that the wings form helically between these wing orientations, and in that the bone anchoring element is not screwed into the bone, but hammered in.

The structure of a helical arrangement of two wings, which are arranged around a mainly cylindrical core, offers the advantage that the bone anchoring element is rotationally stable in the bone. Conventional pedicle screws are not. Corrective rotational moments can also be introduced into the bone using the structure according to the invention, which was previously not possible with pedicle screws.

If the bone anchoring element with the fork head is fixed to a connecting rod using an adjusting means, such as a grub screw, polyaxial pivotability of the fork head is also deactivated. Due to the rotational stability in the bone and the switched off polyaxiality, such a bone anchoring element is resistant to pulling out in the bone. This is because a pull-out movement would force a rotation of the bone anchoring element. This rotation is not possible due to the connection of two or more bone anchoring devices along a connecting rod. Two or more bone anchoring devices along a connecting rod hold the connecting rod in a rotationally fixed manner around the anchoring points and, as a consequence, the bone anchoring element remains firmly seated in the bone.

Additional teeth are advantageous to increase the pull-out strength in the bone. These teeth are preferably located in the pedicle area, so that they can engage with the bone or with the inner wall of the pedicle in order to counteract a pull-out movement on the bone anchoring element with optimum efficiency. For locking, it is advantageous that the teeth are arranged on at least one elastic tongue. With the aid of the resilient tongue, the teeth can give way during the introduction of the bone anchoring element into the interior of the core. They are deformed inward by the bony structure. After the bone anchoring element has been introduced into the pedicle canal, the tongues can be brought into the starting position with the aid of a sleeve element. As a result, the teeth are pressed into the inner wall of the pedicle canal. The bone anchoring element is then locked to the bone in the pedicle area. It is also advantageous if the teeth are arranged laterally, that is, they engage in the pedicle canal in a medial and lateral direction. Only there do they have contact with the cortical layer of the pedicle canal.

To further increase the pull-out strength, it is advantageous if there are one or more circumferential grooves on the core and the grooves have a profile in the circumferential direction which is hook-like or barb-like. This means that the direction of insertion is simplified and an extraction movement is made more difficult. It is advantageous if the circumferential grooves are not partially but completely formed. They cross the lateral wings and contribute to a porosity of the wings.

A porosity of the wings is enormously advantageous for the success of the implant if it is to function without additional bone cement.

Bone cells grow more slowly, and the associated metabolism is interrupted with solid implants. Therefore, a porous structure is very beneficial. Preferably, a porosity of the wings should be selected which is known for the fact that bone cells grow and proliferate. This is a range from 0.2 mm to 2.0 mm, ideally between 0.4 mm and 0.8 mm.

For the bone anchoring element according to the invention to become a functional unit, i.e. a bone anchoring device, it must be mounted with a fork head. Since the lateral wings have a specific width, such a bone anchoring element cannot be guided into the fork head and mounted from the proximal end. The bone anchoring element must be inserted and mounted from the distal end of the fork head so that the bone anchoring device can function as an implant. There is extensive prior art for this type of fork head mounting on bone anchors from the distal side. As an example shown here and not in further detail, a slotted pressure piece is shown, which is guided from the distal into the fork head and then the ball head of the bone anchoring element can be clicked into the pressure piece from the distal side. If a force is now generated, for example by tightening an adjusting means (grub screw) and connecting rod, this force also acts on the pressure piece. The pressure piece is pressed around the ball head by an outer conical surface of the pressure piece and a congruent inner surface of the fork head. A force that is generated by the adjusting means causes the fork head to be fully jammed and polyaxiality to be fixed.

The bone anchoring element is characterized in that it has two lateral wings along the core. These wings have a helical course about the central axis of the core. A pitch between 100 mm to 300 mm is provided, in particular 150 mm to 250 mm, in particular 160 mm to 200 mm. Ideally, the entire range of bone anchoring devices has the same pitch, so that if a bone anchoring device has to be replaced which a different length or diameter, the same pre-prepared canal in the bone can be used. Across all lengths of the bone anchoring device set, the rotation of the helical outer wings is 60° to 120°, in particular 70° to 110°, in particular 80° to 100°. It is also advantageous if an assortment of bone anchoring devices with different lengths and diameters have the same form factor.

The bone anchoring device is to be implanted such that the wing orientation of the distal end of the bone anchoring element corresponds to the main orientation of the pedicle canal. This almost corresponds to a cranial-caudal alignment. The bone anchoring element is driven into the pedicle canal by means of hammer blows. The bone anchoring element rotates about the central axis according to the previously defined pitch. In the final position, the distal wing orientation has a lateral-medial orientation, wherein the proximal wing orientation corresponds to the main pedicle orientation.

After the implantation, the bone anchoring element is located in the vertebra. In the proximal area, the outer wing surfaces are supported on the cranial and caudal areas of the pedicle canal, or they point in these directions. Distally, the projected surface which results from the nucleus and the lateral wing surfaces is supported in the cancellous bone of the vertebra toward the cranial/caudal areas. This prevents tilting of the bone anchoring device when initiating a flexion/extension movement. The bone anchoring device is optimally supported on the bony structures, or at least points in this direction, and distributes the resulting load more homogeneously and across a wider area than a pedicle screw to the cancellous bone tissue. Likewise, the bone anchoring device is proximally supported cranially and caudally in the mainly oval pedicle canal, or it points in this direction with the outer wing edges. Other pedicle screws are located as a cylindrical objects not in the biomechanical optimum in an oval tunnel (=pedicle canal).

To prevent the outer wing surfaces from pressing or even cutting into the caudal and cranial areas of the pedicle area at the proximal area, it is advantageous if the outer surfaces of the wings have convex curvatures in order to reduce the contact stresses with the cranial and caudal pedicle areas.

For a better load distribution of the bending moment along the bone anchoring element, it is advantageous that the two wings taper towards the ball head in the proximal area and end on the outer contour of the core. Furthermore, the sections of the core can run conically in the proximal area, more precisely, in the neck area. This also distributes the bending moments and stresses better in the loaded component.

Naturally, the pedicle canals have a certain form factor which describes the oval. This form factor defines the relationship between height and width. Optimally, the bone anchoring elements according to the invention are precisely adjusted such that they best reproduce the oval cross section. The bone anchoring elements with the two wings having a height (H) that is defined between the outer edges of the wings, and an outer diameter (D) of the core (including teeth), have a form factor with the ratio H/D which is between 1.3 to 2.5, preferably 1.4 to 2.2, preferably 1.6 to 2.0.

Providing a cannulation with lateral openings is advantageous for an additional increase in strength and as a last clinical remedy if the bone quality is too low. Bone cement can be injected through this. It is advantageous here that the orientation of the lateral openings after the implantation always points to cranial and caudal, where the greatest load within the cancellous bone is directed. It also proves to be advantageous if the cannulation has different diameters. In this case, for example, a sleeve element can be inserted from the proximal end.

Since the bone anchoring element according to the invention is a relatively complex geometric structure as part of the bone anchoring device, it is advantageous if the bone anchoring element is manufactured in one piece using a generative manufacturing process. This includes all known 3D printing processes, such as laser beam melting, electron beam melting, or other additive methods. Suitable materials are all implantable materials such as: titanium, CoCr, or stainless steel alloys, or plastics such as PEEK, PSU, PPSU, PEAK, PEK, fiber-reinforced CFR-PEEK, etc. Furthermore, it can be advantageous if geometrical structures with tight tolerances, such as the ball head, can be subsequently reworked using an abrasive process (e.g. CNC turning, CNC milling, or eroding).

Other features and details of the invention can be derived from the patent claims, the following figures and the following description of the illustrated embodiments of the bone anchoring device according to the invention:

Figure 6:
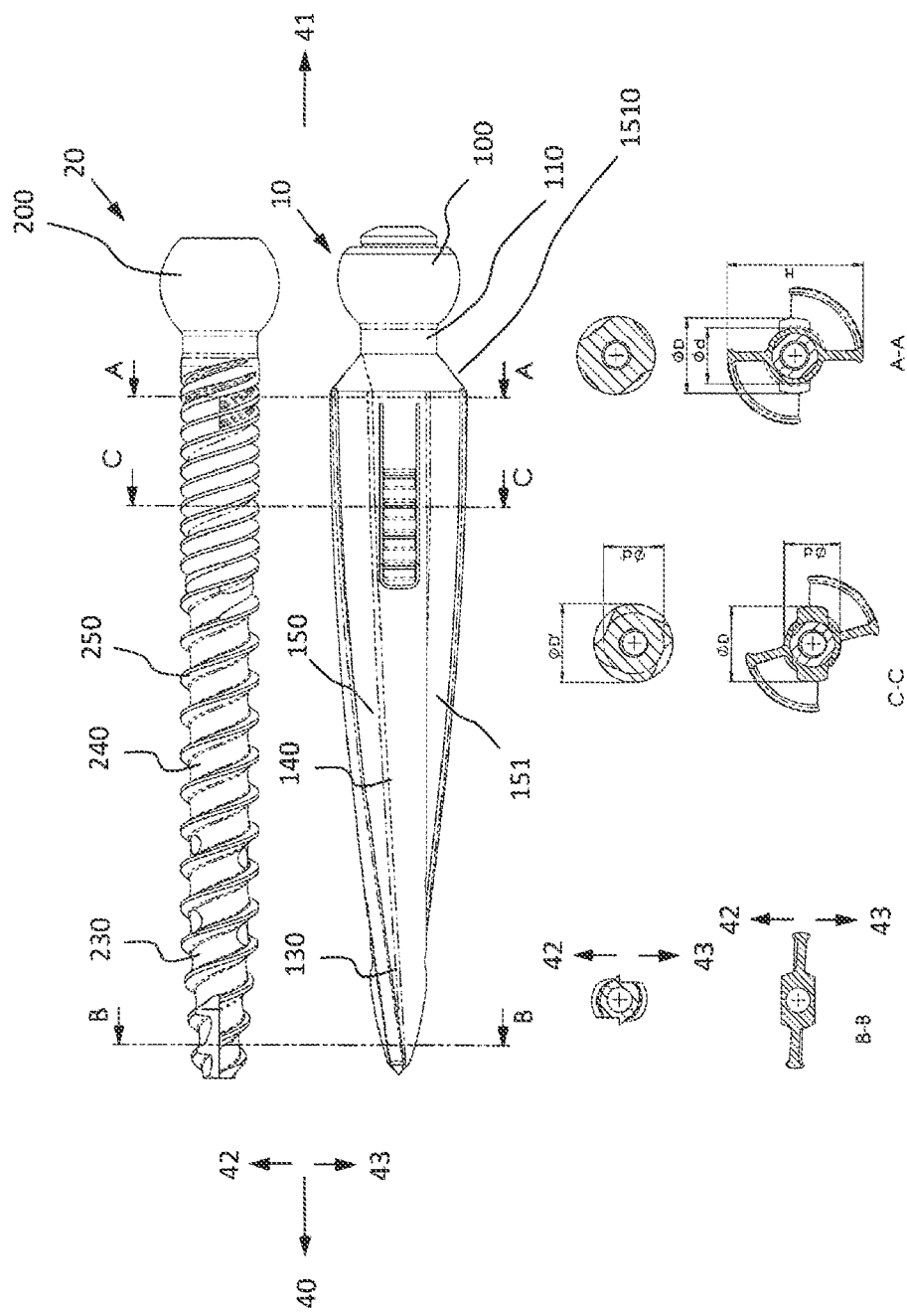

FIG. 6 compares a conventional screw shaft of a bone screw, as is used in a pedicle screw, with the bone anchoring element according to the invention.

Figure 7:
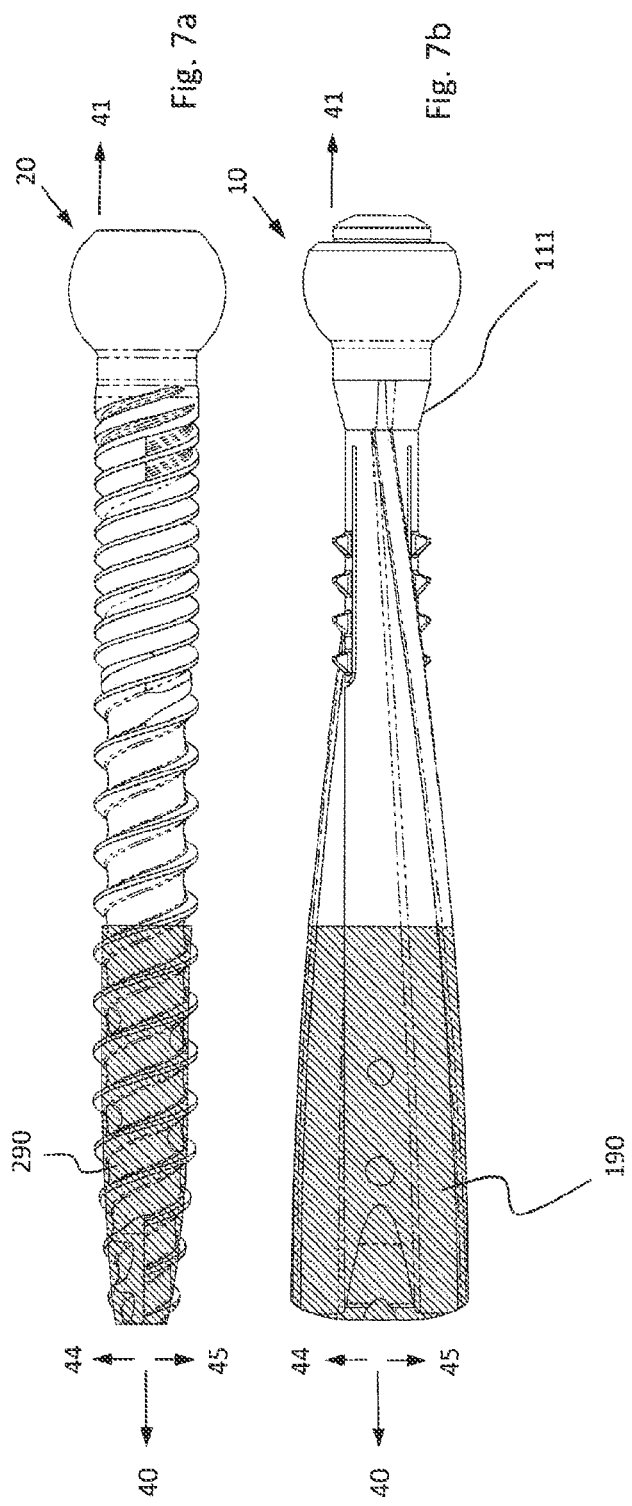

FIGS. 7a and 7b show the associated projected areas which effect the load distribution to the bone tissue.

Figure 8:
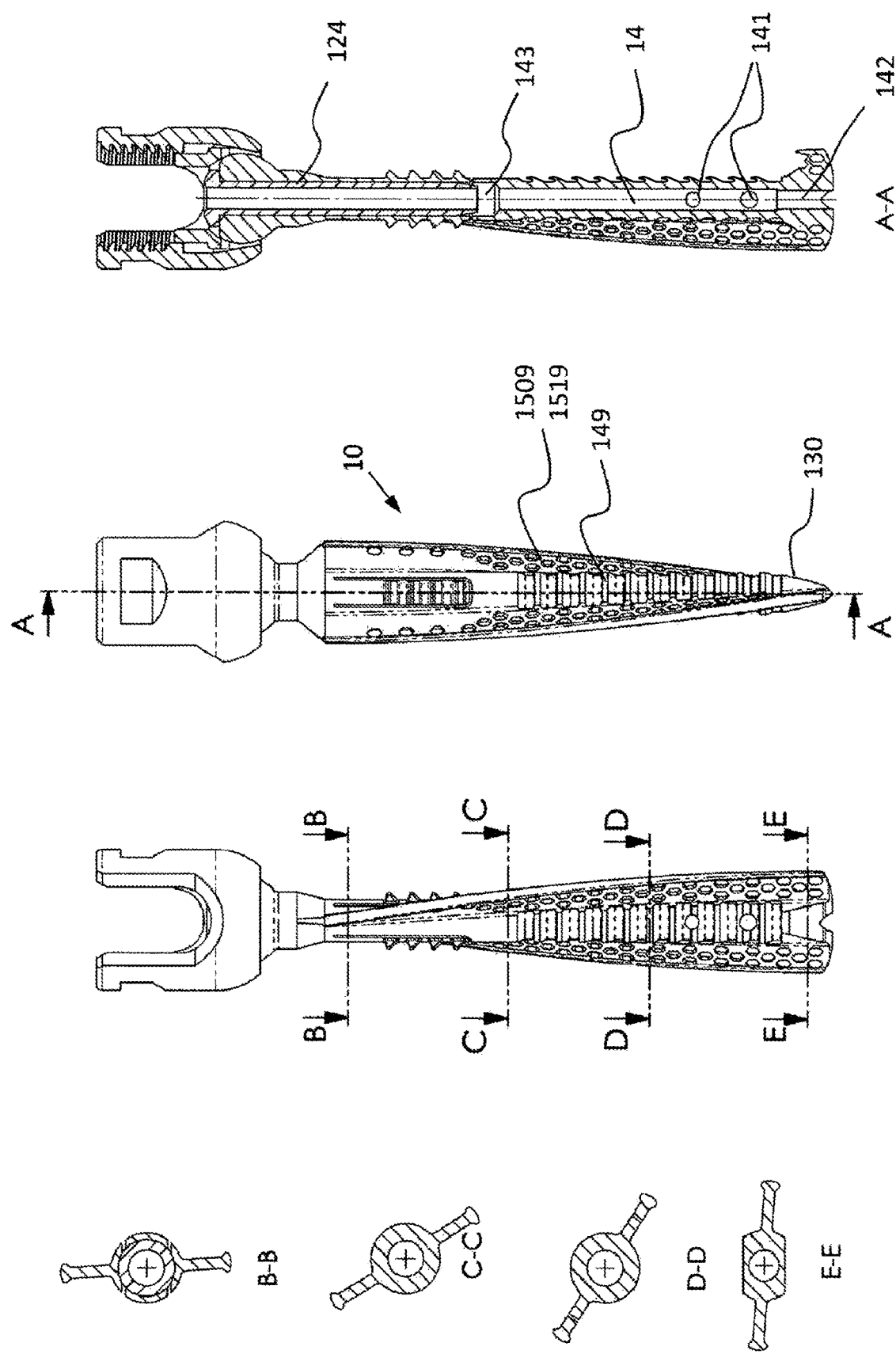

FIG. 8 shows various sections through the bone anchoring device.

Figure 9:
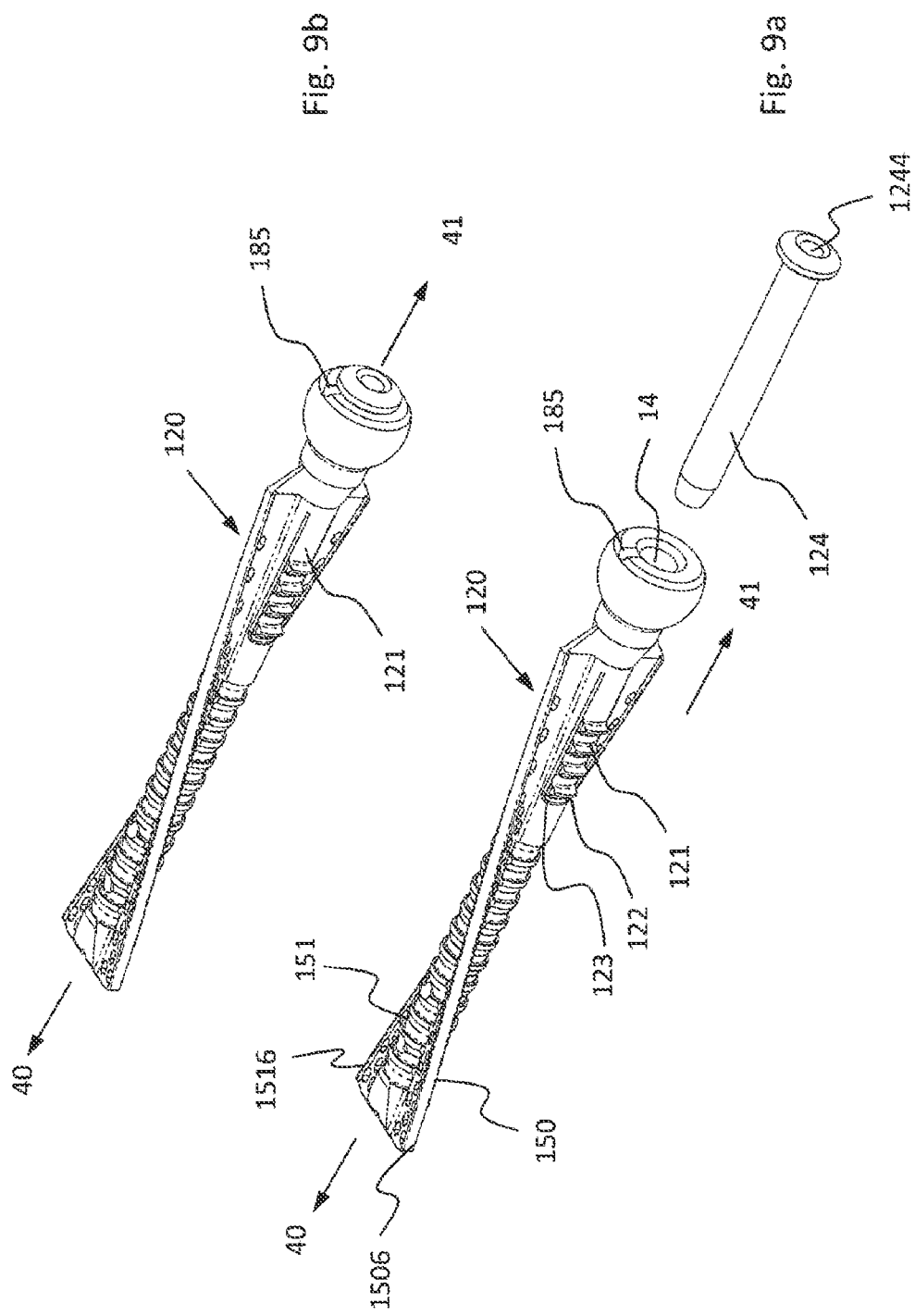

FIGS. 9a and 9b depict the bone anchoring element according to the invention, which has teeth for locking in the pedicle canal, and the sleeve element which presses the elastic tongue with the teeth in the direction of the inner wall of the pedicle.

Figure 10:
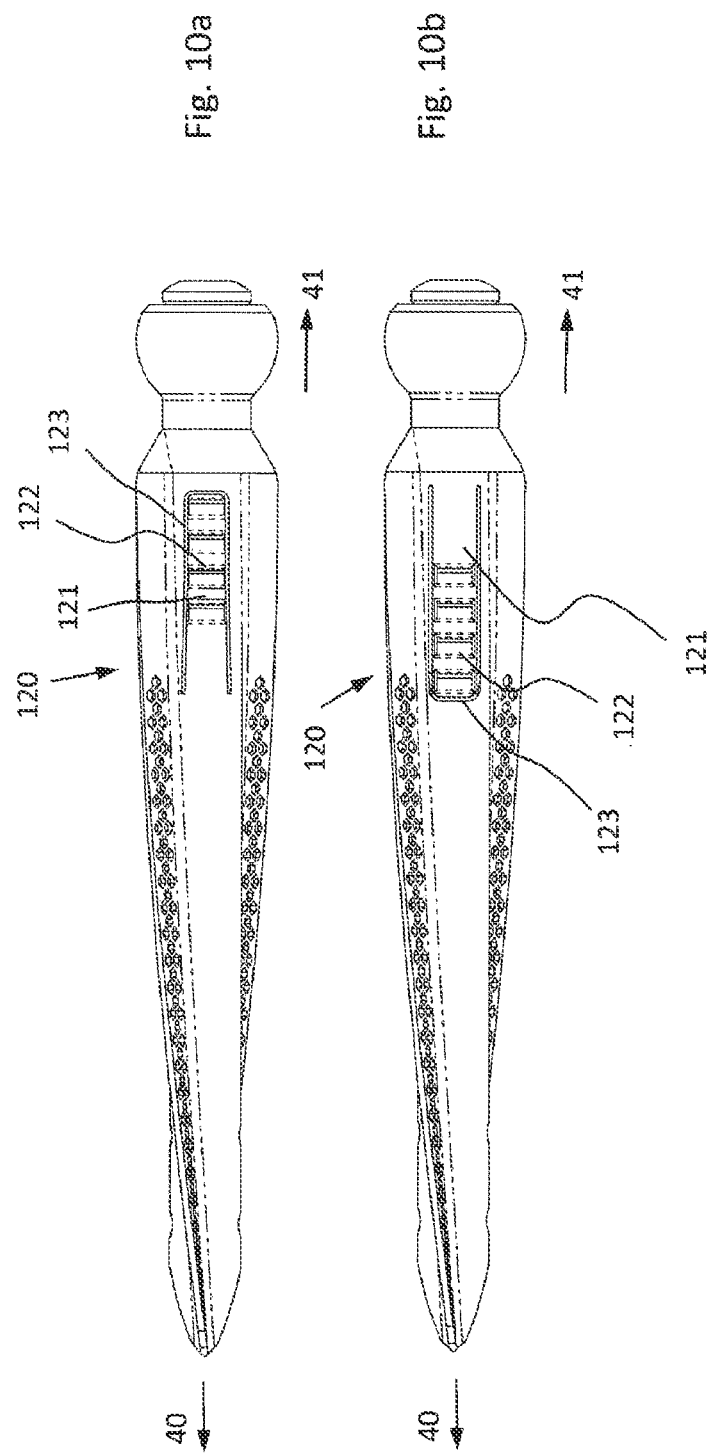

FIGS. 10a and 10b each show a bone anchoring element, wherein the elastic tongue points to the proximal area once and to the distal area the other time.

Figure 11:
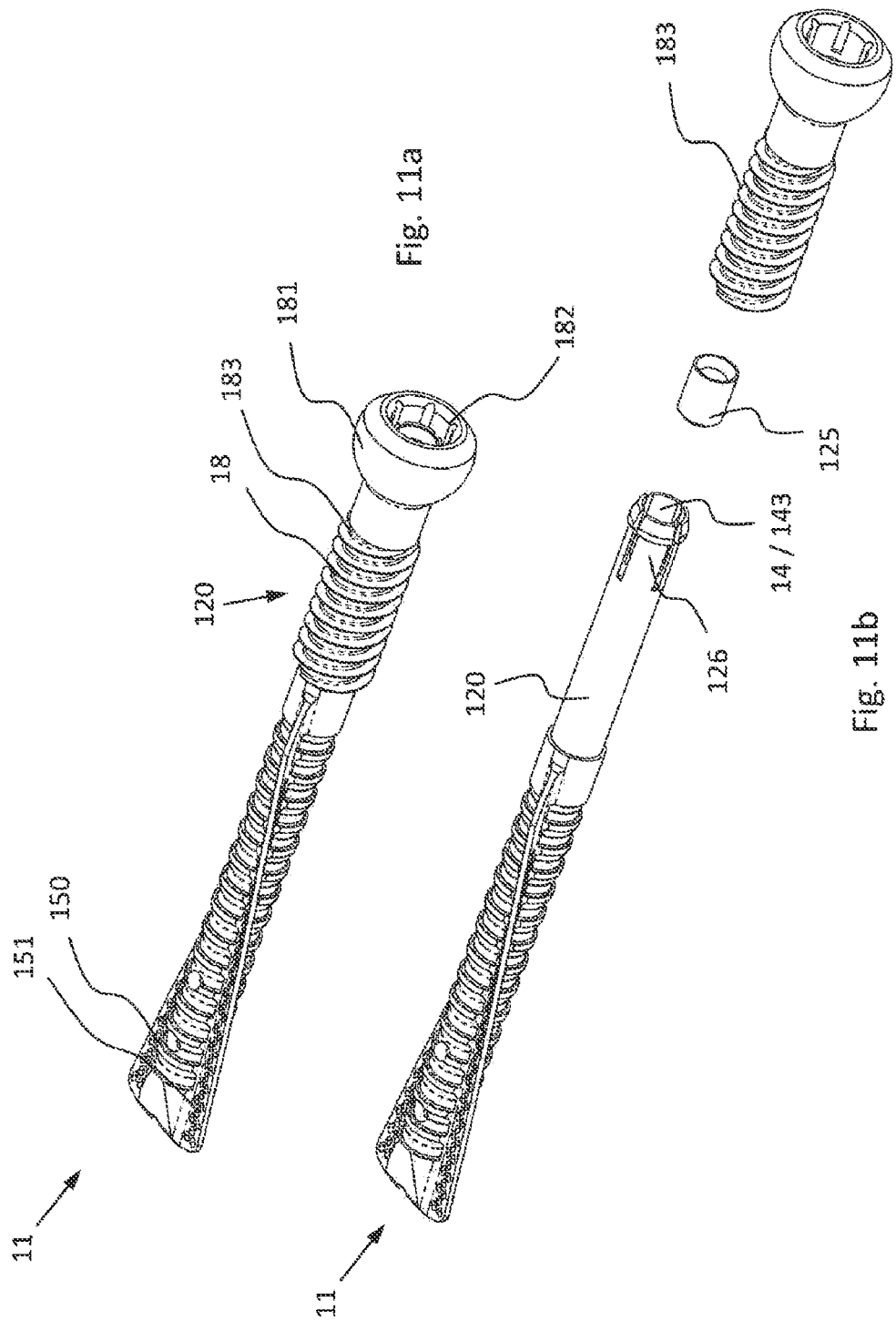

FIGS. 11a and 11b show a bone anchoring element with a rotatably mounted threaded bone section in the pedicle area.

Figure 12:
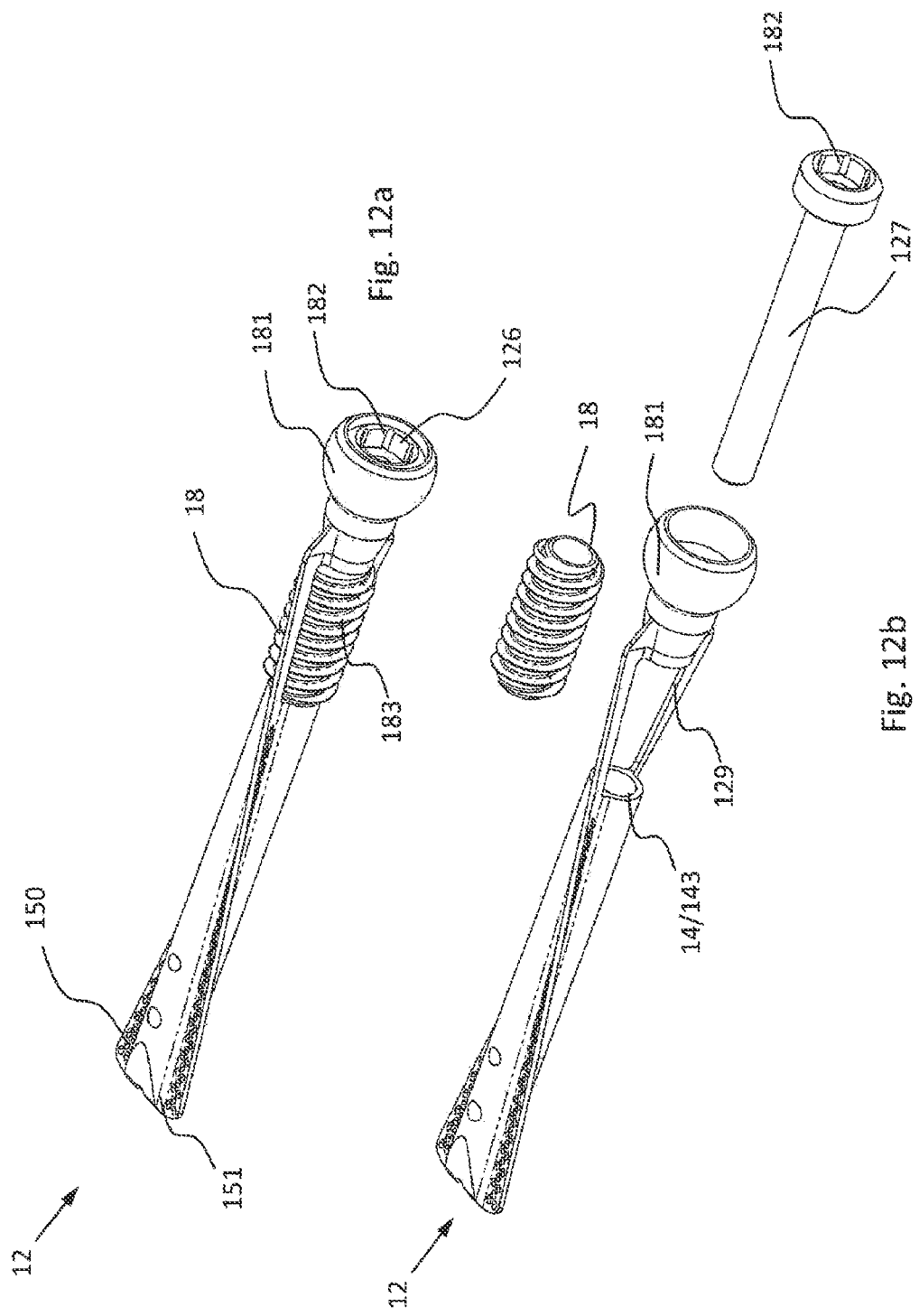

FIGS. 12a and 12b also show a variant which has a rotatably mounted threaded bone section.

Figure 13:
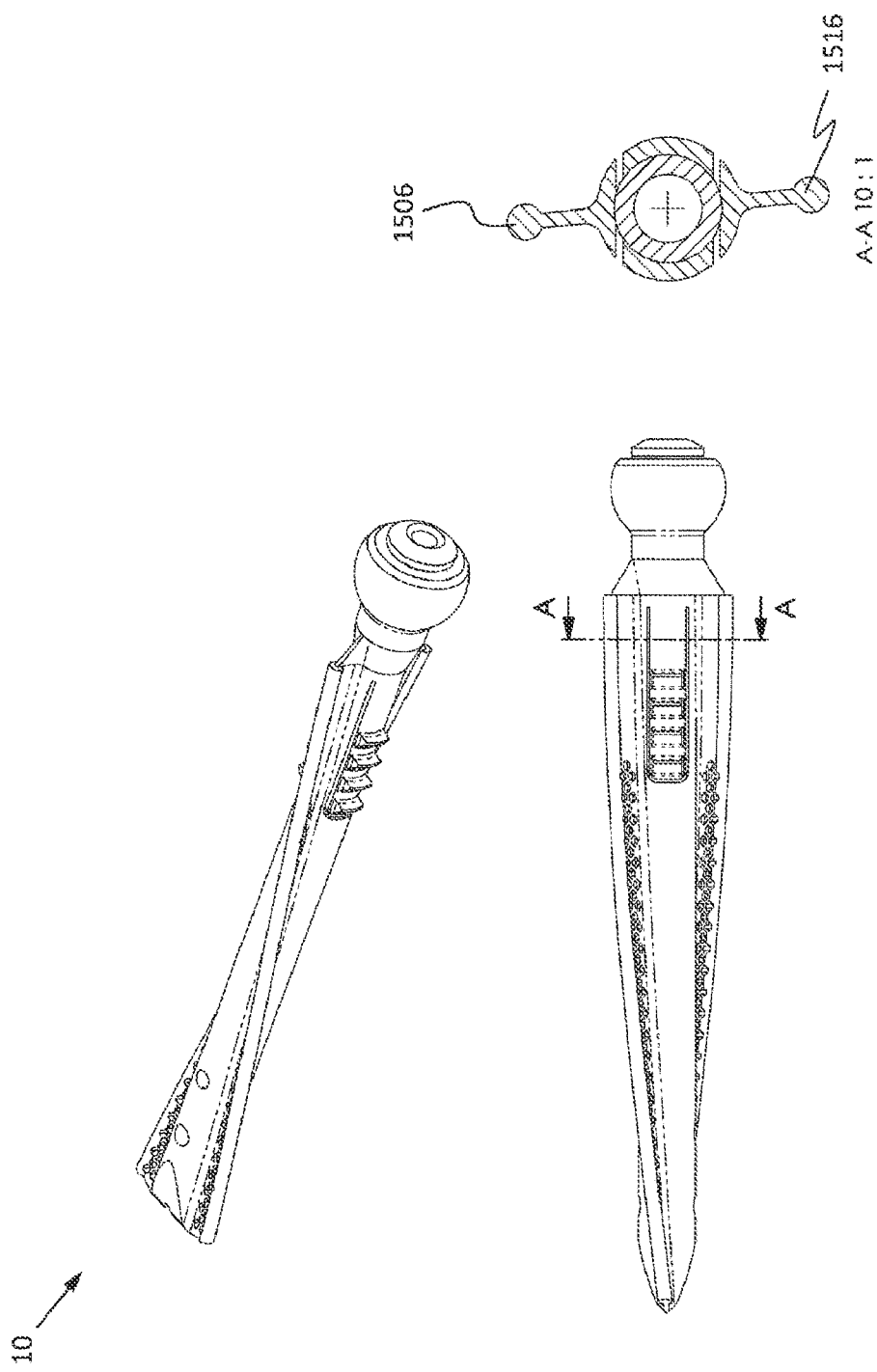

FIG. 13 shows a bone anchoring element in which the outer surfaces of the wings have convex curvatures, such that no stress concentrations arise on the cranial and caudal inner walls of the pedicle.

Figure 14:
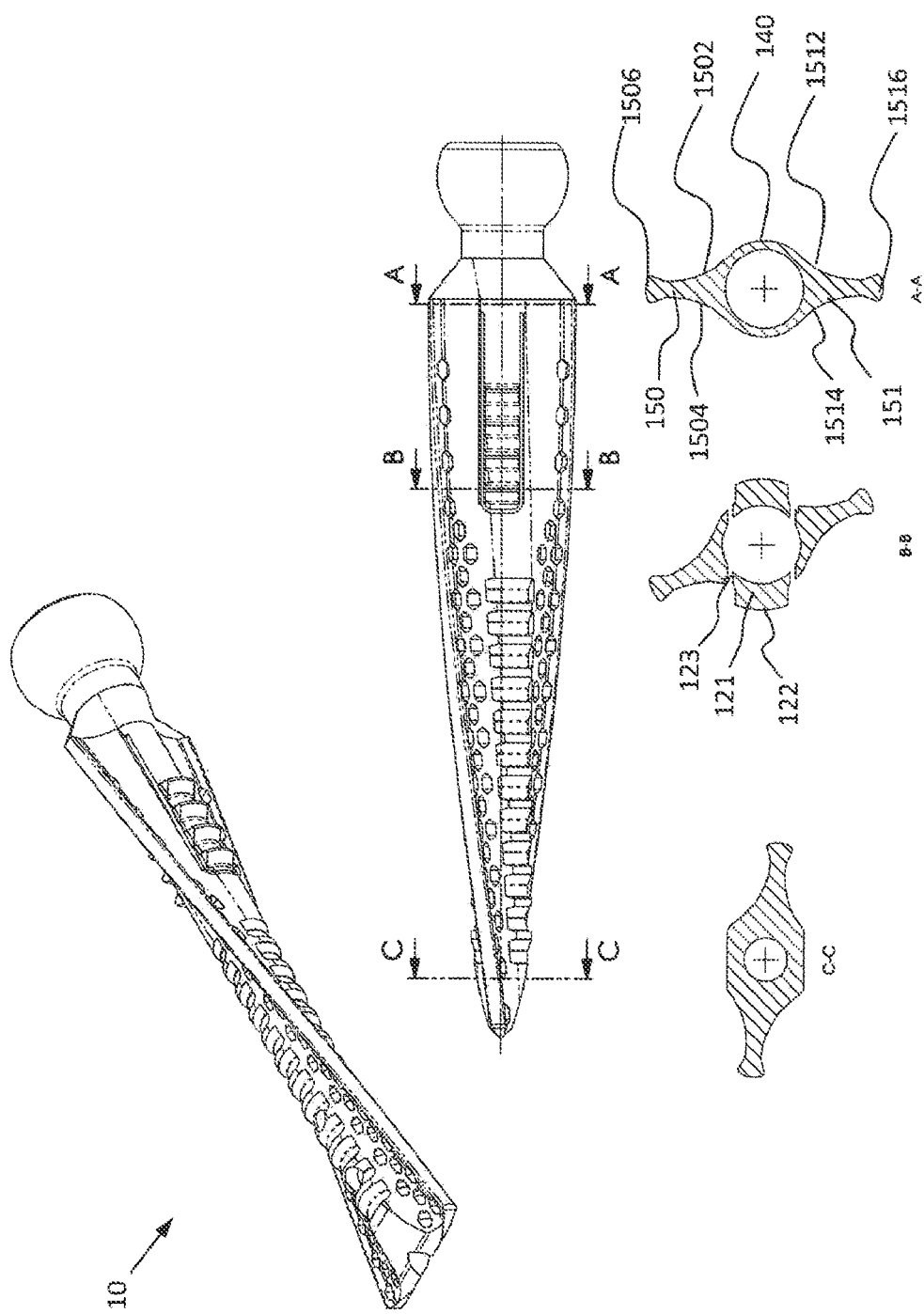

FIG. 14 illustrates a bone anchoring element in which the opposing wing surfaces do not run parallel, but rather thicken towards the core. This has a positive influence on the bending stability of the wings.

Figure 1:
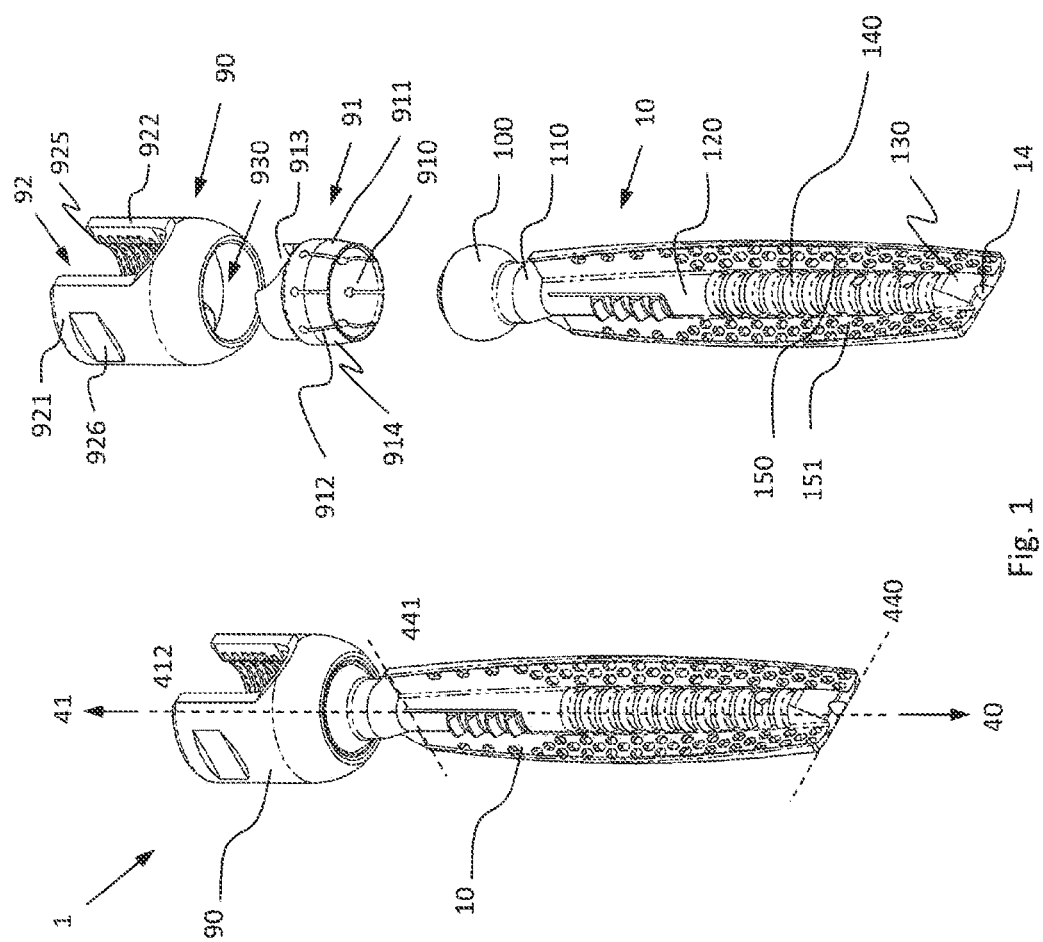
FIG. 1 shows an exploded view of the bone anchoring device according to the invention in the assembled state.
Figure 2:
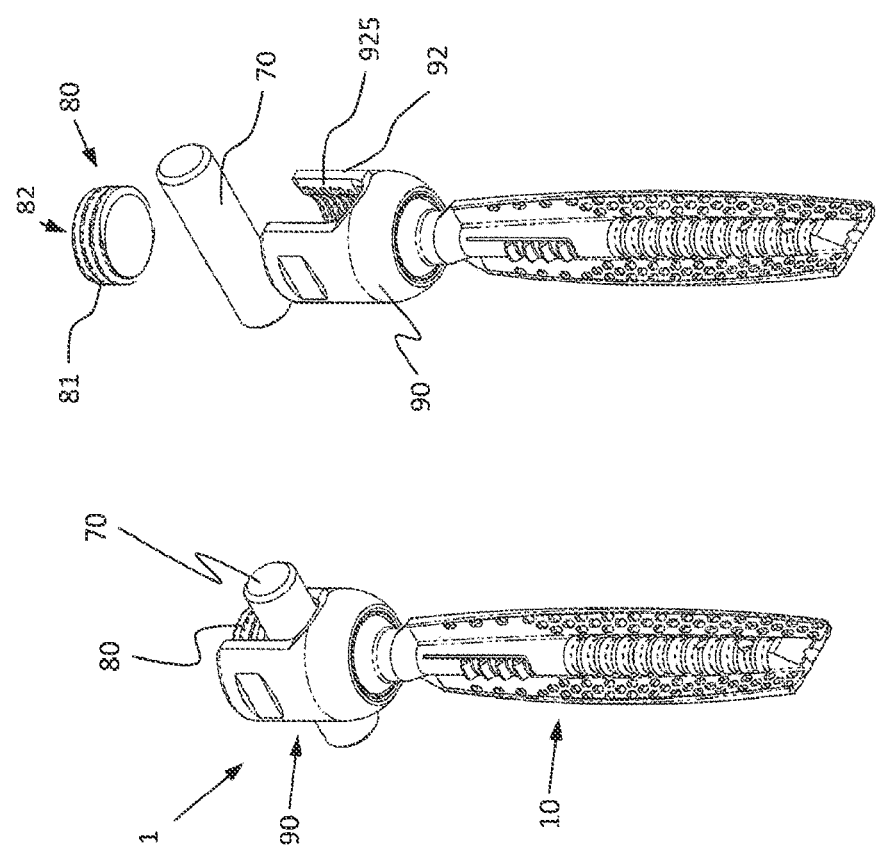
FIG. 2 shows the bone anchoring device according to the invention assembled with a connecting rod and an adjusting means. This in an exploded view of the assembled state.

FIGS. 1 and 2 show the bone anchoring device (1) according to the invention, consisting of a fork head (90), a bone anchoring element (10) and a pressure piece (91). The bone anchoring element (10) defines a central axis along the length (412) which extends from distal (40) to proximal (41). The bone anchoring element (10) has, from proximal (41) to distal (40), a spherical head (100), a neck area (110), a pedicle area (120), a core (140), and a distal area (130). Two wings (150, 151) are arranged laterally along the central and mainly cylindrical core (140). The wings each have one wing orientation in the proximal (441) and distal (440) directions, which are different from one another. Along these two wing orientations (440 and 441), the wings are shaped like a helix according to a larger pitch. Details of the pitch were disclosed above. The bone anchoring element (10) is held by a pressure piece (91) which partially surrounds the ball head (100) and receives it in a seat (910). This seat (910) is elastically deformable in that spring arms (911) are formed by respective slots (912). On the outside, the pressure piece has a conical surface (914) which is in contact with the opening (930) of the fork head (92). The pressure piece (91) is in the fork head (90) in the finally assembled state. The pressure piece (91) proximally has a seat (913) for a connecting rod (70).

This seat (913) is aligned with respect to the fork head (90) in such a way that the U-shaped cutout (92) corresponds to it. The fork head (90) has two tapering legs (921 and 922) in the proximal area, which together form a threaded section (925) into which an adjusting means (80) with a congruent threaded area (81) can be screwed. For this purpose, the adjusting means (80) has a tool port (82), which is not shown. Torx, multi-tooth, hexagon, square ports, etc. are suitable for the tool port (82). The fork head (90) has devices (926) on the outer proximal circumference, such as, for example, a retaining groove or indentations, which are suitable for attaching an instrument to it.

Figure 3:
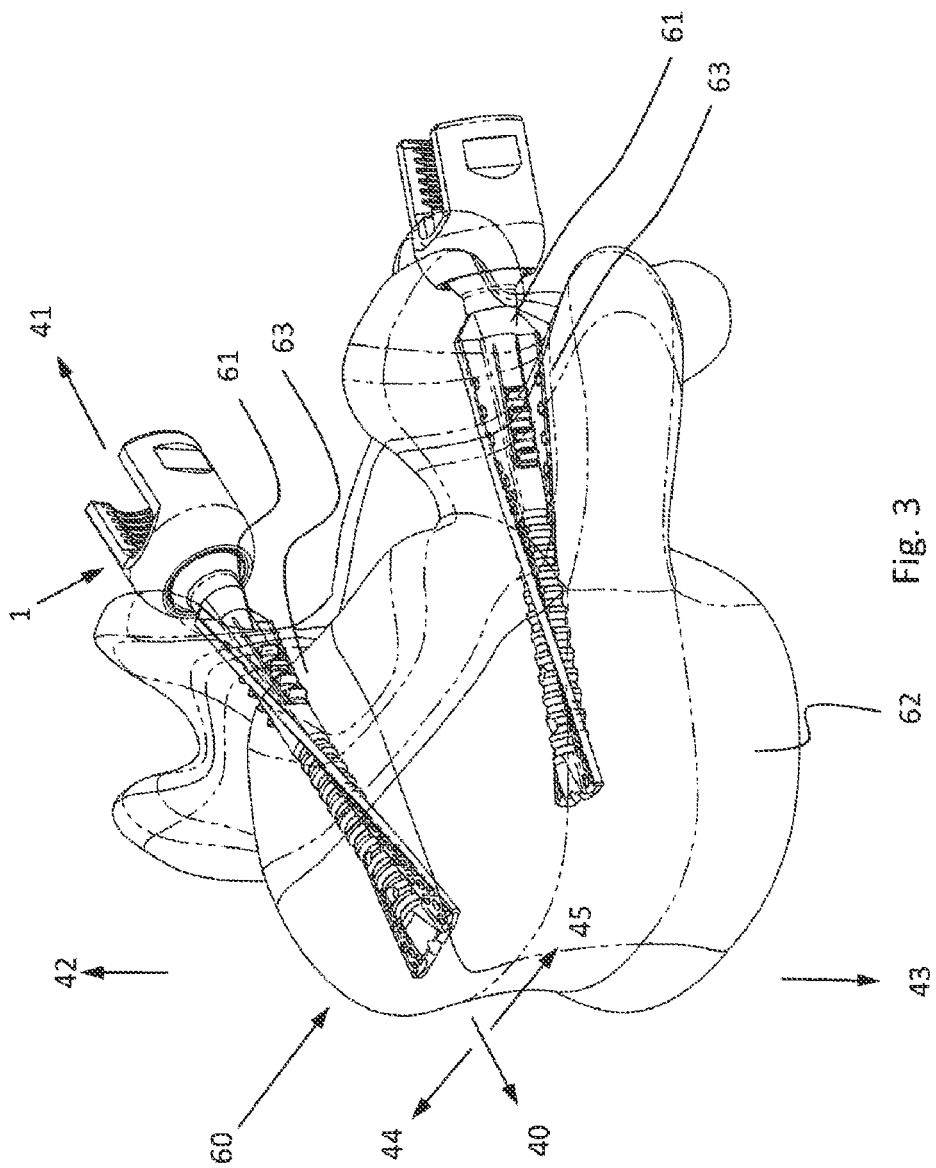
FIG. 3 illustrates two bone anchoring devices implanted in a vertebra.
Figure 5:
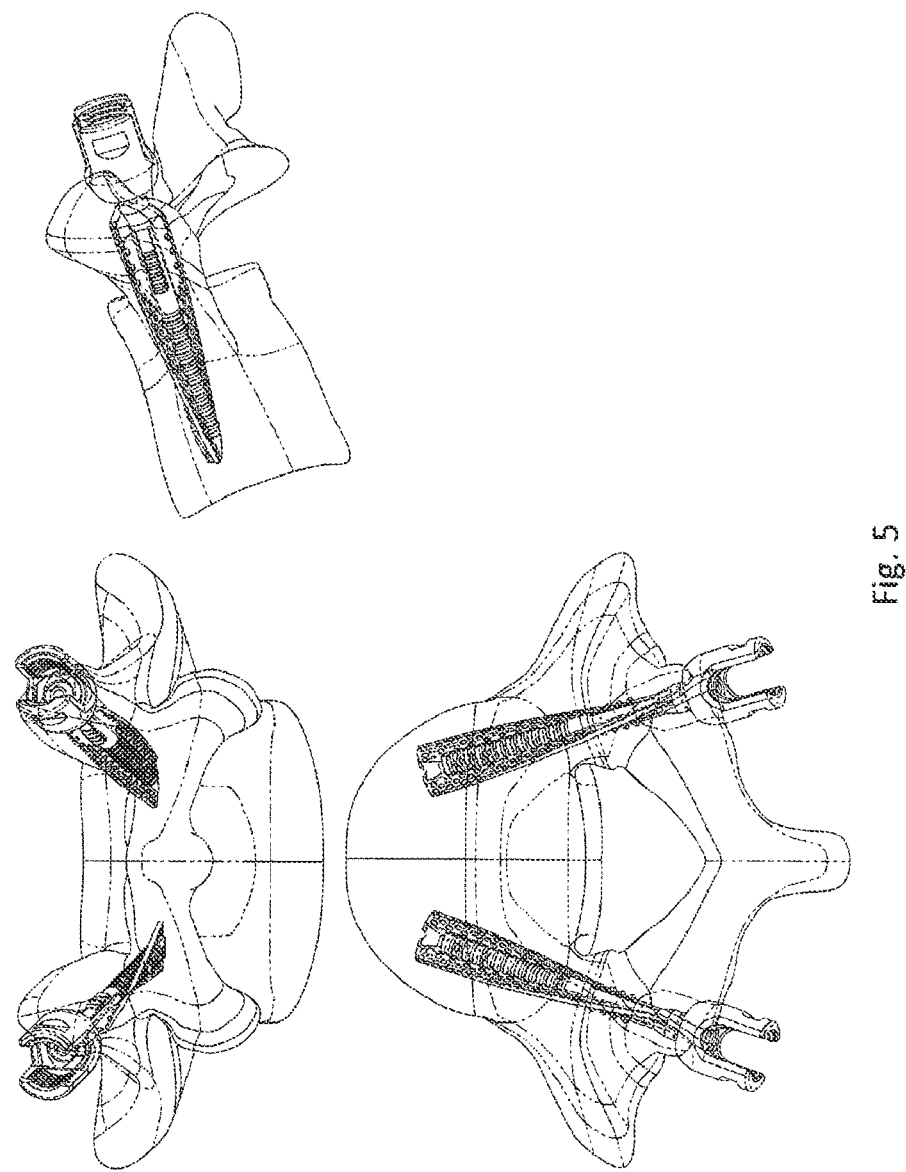
FIG. 5 shows three views of the vertebra with two implanted bone anchoring devices.

FIGS. 3 and 5 show a pair of bone anchoring devices (1) implanted in a vertebra (60). Different anatomical directions can be defined in this case. Distal (40) and proximal (41) areas result from the definition mentioned above. The lateral (44) and medial (45) directions are defined laterally and the cranial (42) and caudal (43) directions are defined vertically. The vertebra (60) can be divided into regions that are important for the bone anchoring device (1) according to the invention; pedicle entrance (61), pedicle canal (63), and the internal cancellous bone (62).

Figure 4:
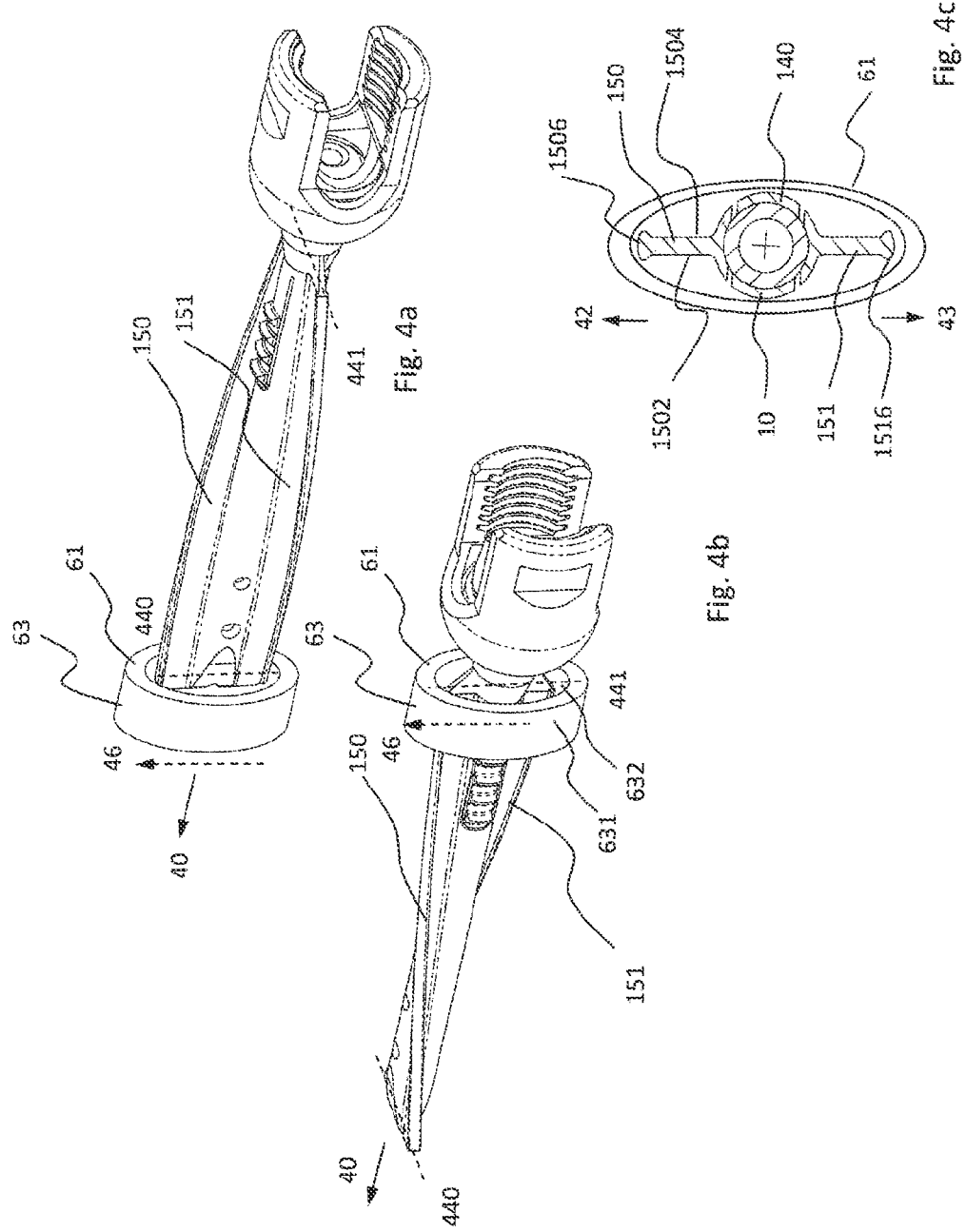
FIG. 4a shows the bone anchoring device before it enters the pedicle canal.
FIG. 4b shows the bone anchoring device after implantation in the final position.
FIG. 4c shows a cross section through a pedicle canal with an implanted bone anchoring device.

FIGS. 4a, 4b, and 4c show the process of implantation in the pedicle canal (63). The pedicle canal (63) has a cortex (631) and an internal cancellous area (632). It is visible in FIG. 4a that the distal end of the bone anchoring element (10) is guided into the pedicle entrance (61). The pedicle canal has an oval shape in section (FIG. 4c), wherein the longer extension of the oval is oriented in the cranial-caudal direction (42, 43). This corresponds to the pedicle orientation (46). When inserting the bone anchoring element (10) into the pedicle entrance (61), the surgeon must ensure that the distal wing orientation (440) matches the pedicle orientation (46). After the bone anchoring element (10) has been hammered into the vertebra (60) (FIG. 4b), the proximal wing alignment (441) now matches the pedicle alignment (46). That is that the profile of the bone anchoring element (10) remains identical in the pedicle canal (FIG. 4c) in a sectional view. The bone anchoring element (10) moves during the implantation into the vertebral interior (62) along the predetermined helix which is forced by the wings (150, 151). In the completely implanted state, the distal wing alignment (440) is in a lateral alignment, i.e. the wings (150, 151) point to the lateral and medial areas. FIG. 4c also shows that the bone anchoring element (10) approximates the oval area of the pedicle (63) quite well. Cranially (1506) and caudally (1516), the bone anchoring element (10) preferably has rounded outer surfaces which prevent the cortical layer of the pedicle from being cut, indented, or split. The outer surfaces (1506, 1516) can protrude over the side walls of the wings (1502, 1504 and 1512, 1514).

FIG. 6 shows a direct comparison of a conventional bone screw (20) and the bone anchoring element (10) of the bone anchoring device (1) according to the invention. The ball head (100, 200) and neck area (110, 210) are structurally similar. Both bone anchors (10 and 20) have a core (140 and 240) and a distal area (130 and 230). A bone thread (250) is provided in the bone screw (20), which at the same time defines the outer diameter (D') of the bone screw. The core (240) corresponds to the inner diameter (d'). Likewise, the outer diameter (D) can be located on the bone anchoring element (10) on the basis of the outer circumference of the teeth (122). Furthermore, the core diameter (d) can be defined by the core (140) itself. The diameters thus equal D'=D as well as d'=d for a direct comparison. As a clearly recognizable difference to the bone screw, the bone anchoring element (10) has two wings, a first wing (150) and a second wing (151). These wings define a width (H). The ratio of the width (H) to the diameter (D) is defined as the form factor. The preferred ranges of the form factor have been mentioned above. It is advantageous if the width of the two wings (150, 151) gradually decreases towards the spherical head (100) (1510) and ends in the core (140). This has a positive effect on the bending stress curve.

FIGS. 7a and 7b illustrate the direct comparison of the load-bearing projected areas (190, 290) in the cancellous bone (62) of a vertebra (60). FIG. 7a shows the projected area (290) of a bone screw (20), which during a flexion/extension movement is loaded within the cancellous bone. FIG. 7b shows the projected area of the bone anchoring element (10) according to the invention. It can clearly be seen that this area (190) is significantly larger than the area of a bone screw (290). The larger this projected area, the more load can be transferred to a soft cancellous tissue. Overall, depending on the form factor, it can be assumed that this active load-bearing area will almost double. In this receiving direction, the advantageous course of an increase in diameter (111) can be identified between and/or at the pedicle area (120) and the neck area (110). This ensures that the neck area has sufficient flexural rigidity. The increase in diameter can be conical, conical in sections, or based on curves.

FIG. 8 shows two views of the bone anchoring device (1) according to the invention as well as some sections orthogonal to the central axis (412). It can be seen that the wings (150, 151) have a different orientation. The cannulation (14) with the lateral fenestration openings (141) can be seen in the longitudinal section. The cannulation preferably has different diameters (142, 143). On the one hand, this is intended to increase fluid resistance at the distal end of the cannulation by reducing the diameter in the distal direction (142). On the other hand, it is advantageous if the cannulation (14) can also be used as a seat for a sleeve element (124). A diameter enlargement (143) can be provided for this purpose. In a view of the bone anchoring device (1), it can be seen that the wings (150, 151) are characterized by a porosity or by several openings (1509, 1519). These are used for the growth and integration of bone cells. A preferred pore size has already been mentioned. It is also advantageous if the core (140) has one or more circumferential grooves (149). These grooves have a profile similar to a hook. This improves the pull-out strength of the bone anchoring element (10) in the bone.

FIGS. 9a and 9b show the bone anchoring element (10) using a sleeve element (124) which can be inserted into the cannulation opening (14). FIG. 9a shows the state in which the elastic spring arms (121) with the teeth (122) on them can compress into the interior of the core. The elastic spring arms (121) are formed by one or more slots (123). Shown here are U-shaped slots. After the sleeve element (124) has been inserted into the cannulation (14) (FIG. 9b), the elastic spring arms (121) can no longer compress. The sleeve element body (124) prevents them from compressing. Furthermore, by inserting the sleeve element (124), an active displacement of the elastic spring arms (121) from the cannulation area is achieved. Thus, it is possible for the teeth (122) to be pressed into the pedicle wall after the implantation of the bone anchoring element (10) with the aid of the insertion of the sleeve element. Ideally, the teeth (122) are at the level of the pedicle area (120). In this area (120), they can achieve the best possible effect of locking with the pedicle canal (63).

FIGS. 10a and 10b show a different direction in which elastic spring arms can be arranged. Also shown in FIGS. 9a and 9b is an indicator (185) which is used for the distal wing alignment (440) and/or for indicating proximal wing alignment (441) to the user. As an indicator, asymmetrical shapes, slits, deposits, or even labeling can be useful. Furthermore, it is advantageous if the indicator simultaneously serves as an interface for a surgical instrument and thereby indicates the orientation of the wing orientations (440, 441) away from the implant.

FIGS. 11a and 11b show an alternative embodiment of a bone anchoring element (11). The pedicle area (120) of the bone anchoring element (11) is cylindrical in shape. Mounted thereon is a rotatable partial threaded section (18) which has a bone thread (183), a ball head (181), and a tool engagement point (182). By initiating a rotation at the tool engagement point (182), the bone thread can be activated, and anchoring in the pedicle area (120) like with a bone screw can be achieved. The advantages of a bone screw can thus be combined with large-area distal support. The rotatable partial threaded section (18) is held by elastic hooks (126). Without a sleeve element (125), the elastic hooks (126) are flexible. Thus, for example, the rotatable partial threaded section (18) can be mounted quite easily by being pushed on. After the sleeve element (125) has been inserted into the cannulation (14, 143), the elastic hooks (126) can no longer be moved, thereby creating loss prevention.

Another alternative embodiment is shown in FIGS. 12a and 12b. A bone anchoring element (12) is shown which has a rotatable partial threaded section (18). This threaded section (18) is located in an opening (129) provided for this purpose. Here, too, the threaded section (18) is non-rotatably connected to a tool engagement point (182) via a rotatable sleeve element (127), but it is joined rather than integral. The ball head (181) is formed by the bone anchoring element (12) itself. It is stationary compared to the rotatable sleeve element (127).

FIG. 13 shows a shape of a bone anchoring element (10) in which the rounded edges of the outer wing edges 1506 and 1516 are shown more with more emphasis. Convex curved surfaces on the outer edges have the advantage that they do not cut into the bone and that loads are distributed more homogeneously. It can definitely be advantageous for the width of the convexly curved outer wing edges to be greater than the width of the lateral wing surfaces (1502, 1504, 1512, and 1514).

FIG. 14 shows an advantageous embodiment of the bone anchoring element (10) according to the invention in which the wings (150 and 151) do not run parallel to the core (140), but rather thicken in section. As a result, bending stresses are distributed more homogeneously radially outwards. Furthermore, it can also be seen here that the lateral surfaces of the wings (1502, 1504, 1512, and 1514) can have a smaller distance than the convex outer edges (1506 and 1516).

The invention claimed is:

1. A bone anchoring device for anchoring and fixing vertebrae, and for insertion into a pedicle canal, with a fork head having a U-shaped cutout in a side view for a connecting rod, the U-shaped cutout including two legs which terminate proximally and form a threaded section which engages with an adjusting means, wherein the legs have a radially outer circumferential area in which at least one retaining groove or other instrument attachment point is formed for gripping the fork head by means of a handling instrument, and a bone anchoring element, having a proximal end in the axial direction, such that a distal direction and a proximal direction are also defined, wherein the bone anchoring element has a spherical head at the proximal end area and the bone anchoring element can be pivoted polyaxially with respect to the fork head, and the bone anchoring element is mounted with the fork head,
wherein the bone anchoring element has a substantially cylindrical core, and in that the core at the proximal area enlarges in diameter at least in sections from distal to proximal, and in that two wings extend laterally from the core and the wings have a distal wing orientation and a proximal wing orientation different from the distal wing orientation, and in that the wings form helically between these wing orientations, and in that the bone anchoring element is not configured to be screwed into the bone but to be hammered in, and in that, after implantation of the bone anchoring element into a vertebra, outer surfaces of the wings at a proximal area point in the direction of the cranial and caudal areas of the pedicle canal and distally, projected area that is formed by the core and lateral wing surfaces, is aligned in the cranial/caudal direction in the cancellous bone of the vertebra.

2. The bone anchoring device according to claim 1, wherein the two wings taper in width at the proximal area towards the spherical head and open onto an outer contour of the core.

3. The bone anchoring device according to claim 1, wherein the bone anchoring element has a pedicle area which has at least one resilient tongue which results from a U-shaped slot, and in that the resilient mobility of this at least one resilient tongue is inhibited by an insertable sleeve element.

4. The bone anchoring device according to claim 3, wherein the resilient tongue has one or more teeth, and in that these teeth communicate with the pedicle canal in the pedicle area and, after insertion of the sleeve element, lock into place with the bone.

5. The bone anchoring device according to claim 1, wherein the bone anchoring element with the two wings defines a height H between the outer edges of the wings, and an outer diameter D of teeth, wherein the form factor, from the ratio H/D, is between 1.6 to 2.0.

6. The bone anchoring device according to claim 1, wherein the bone anchoring element has at least one circumferential groove on the core, and in that the circumferential groove forms a hook-like profile which hooks with the bone in the pull-out direction.

7. The bone anchoring device according to claim 1, wherein the outer surfaces in a section of the wings have convex curvatures in order to reduce the contact stresses with respect to the cranial and caudal pedicle areas.

8. The bone anchoring device according to claim 1, wherein the outer surfaces of the wings, in section transverse to the axis, are wider than the minimum distance between the lateral wing surfaces.

9. The bone anchoring device according to claim 1, wherein the lateral wing surfaces thicken towards the core in section transverse to the axis.

10. The bone anchoring device according to claim 1, wherein the wings have several openings which have a pore size between 0.4 and 2.0 mm, preferably 0.5-1.0 mm, and in that these openings are hexagonal and are used as a hole for the growth of bones.

11. The bone anchoring device according to claim 1, wherein the bone anchoring element is manufactured with the aid of an additive manufacturing method.

12. The bone anchoring device according to claim 1, wherein the distal region of the bone anchoring element has a cannulation and fenestration openings for bone cement augmentation, wherein the cannulation and fenestration openings are oriented cranially and caudally when the bone anchoring element is placed in the vertebra.

13. The bone anchoring device according to claim 1, wherein the distance of the wings between the two wing orientations is between 100 mm to 300 mm.

14. The bone anchoring device according to claim 1, wherein the distal wing orientation is substantially perpendicular to the proximal wing orientation.

15. The bone anchoring device according to claim 1, wherein the fork head has a pressure piece, wherein the pressure piece partially surrounds the bone anchoring element on the ball head, and the pressure piece forms at the distal area at least one slot, in that the pressure piece has a resilient area such that the pressure piece can enclose the ball head in a resilient manner, and in that the pressure piece proximally forms a seat for the connecting rod.

16. The bone anchoring device according to claim 1, wherein the pedicle area of the bone anchoring element has a partial threaded bone section, in that this partial threaded bone section is joined with or connected to a tool attachment point, and in that the threaded bone section is rotatably but fixedly mounted with respect to the bone anchoring element.

17. The bone anchoring device according to claim 1, wherein the bone anchoring element has an indicator which allows inferring the distal wing alignment and/or proximal wing alignment.

18. The bone anchoring device according to claim 11, wherein the additive manufacturing method uses 3-D printing, a laser beam, or electron beam melting.

19. The bone anchoring device according to claim 11, wherein the bone anchoring element is manufactured as a one-piece component.

20. A bone anchoring device for anchoring and fixing vertebrae, and for insertion into a pedicle canal, with a fork head having a U-shaped cutout in a side view for a connecting rod, the U-shaped cutout including two legs which terminate proximally and form a threaded section which engages with a threaded screw element, wherein the legs have a radially outer circumferential area in which at least one retaining groove or other instrument attachment point is formed for gripping
the fork head by means of a handling instrument,
and a bone anchoring element having a proximal end in the axial direction, such that a distal direction and a proximal direction are also defined, wherein the bone anchoring element has a spherical head at the proximal end area and the bone anchoring element can be pivoted polyaxially with respect to the fork head, and the bone anchoring element is mounted with the fork head,
wherein the bone anchoring element has a substantially cylindrical core, and in that the core at the proximal area enlarges in diameter at least in sections from distal to proximal, and in that two wings extend laterally from the core and the wings have a distal wing orientation and a proximal wing orientation different from the distal wing orientation, and in that the wings form helically between these wing orientations, and in that the bone anchoring element is not configured to be screwed into the bone but to be hammered in, and in that, after implantation of the bone anchoring element into a vertebra, outer surfaces of the wings at a proximal area point in the direction of the cranial and caudal areas of the pedicle canal and distally, projected area that is formed by the core and lateral wing surfaces, is aligned in the cranial/caudal direction in the cancellous bone of the vertebra.

\* \* \* \* \*